United States Patent [19]

Brodbeck et al.

[11] 4,448,882

[45] May 15, 1984

[54] STABILIZED PEROXIDASE COMPOSITIONS

[75] Inventors: Hans Brodbeck, Münchenstein; Harald Gallati, Dornach, both of Switzerland

[73] Assignee: Hoffmann-La Roche Inc., Nutley, N.J.

[21] Appl. No.: 397,613

[22] Filed: Jul. 12, 1982

[30] Foreign Application Priority Data

Jul. 30, 1981 [CH] Switzerland .......................... 4944/81

[51] Int. Cl.$^3$ .......................... C12N 9/96; C12N 9/08; C12Q 1/28
[52] U.S. Cl. ..................................... 435/188; 435/28; 435/192
[58] Field of Search .......................... 435/188, 192, 28

[56] References Cited

U.S. PATENT DOCUMENTS 4,252,896 2/1981 Shaffar ..................................... 435/7
4,378,429 3/1983 Modrovich ........................... 435/11

OTHER PUBLICATIONS

Chemical Abstract 92, 2753w (1980).
Chemical Abstract 92, 2753x (1980).
Chemical Abstract 92, 2755y (1980).
Chemical Abstract 90, 99575j (1979).

*Primary Examiner*—Lionel M. Shapiro
*Attorney, Agent, or Firm*—Jon S. Saxe; George M. Gould; John J. Maitner

[57] ABSTRACT

A method for the stabilization of peroxidase in a medium containing a serum or serum protein by the addition of 4-amino-antipyrine and stabilized peroxidase compositions are described.

12 Claims, No Drawings

STABILIZED PEROXIDASE COMPOSITIONS

SUMMARY OF THE INVENTION

The invention relates to a method for the stabilization of peroxidase in a medium containing serum or serum protein by addition of 4-amino-antipyrine thereto.

BACKGROUND OF THE INVENTION

The enzyme peroxidase, especially horseradish peroxidase, has many uses, and of particular importance is its use for labelling of immunological reaction partners, for example, haptens, antigens or antibodies, utilized in carrying out immunological test procedures. Peroxidase is preferably used in immunological test methods since its activity or presence can be readily and simply detected. For this reason, an immunologically-active material to which the peroxidase is bound is an essential ingredient in many commercially available kits used for carrying out enzyme-immune test procedures. Since, before use, such kits are transported over large distances and are stored for various periods of time, it is essential that the activity of the enzyme be preserved for as long a period of time as possible. However, it is known that the enzyme peroxidase is not very stable irrespective of whether it is present in isolated form or is bound to another component, particularly in low concentrations. The storage stability is therefore also low, which detracts from the commercial importance of such kits.

At present, peroxidase conjugates are stored in a reaction medium containing serum or serum protein, which can contain, for example, approximately 20% goat serum. In this connection, it has been shown that the presence of the serum increases the stability of the conjugate. On the other hand, with high storage temperatures (e.g. 37° C.) and/or after a long storage period (e.g. 6 months) it has also been observed that the serum contributes to the inactivation of the peroxidase by cleaving the haemin part from the enzyme. This inactivation of the peroxidase is evidently caused by the haemin interactions between the peroxidase and the haemin-binding proteins of the serum.

In accordance with the present invention, a method is disclosed for reducing the inactivation of peroxidase in a medium containing serum or serum protein and thereby substantially improving the stability of said peroxidase.

DETAILED DESCRIPTION OF THE INVENTION

The present invention relates to the use of 4-amino-antipyrine to stabilize peroxidase in a medium containing a serum or serum protein.

It has been found that the addition of a stabilizing amount of 4-amino-antipyrine to a medium containing serum or serum protein reduces the inactivation of the peroxidase thereby improving the stability of said peroxidase.

The preferred peroxidase used in the method of this invention is horseradish peroxidase.

Examples of serum which can be employed in the method of this invention are goat and foetal calf serum, goat serum is the preferred serum.

Albumin is an example of a serum protein which can be used in the method of this invention.

The stabilized peroxidase compositions of this invention comprise peroxidase in a medium containing serum or serum protein and a stabilizing effective amount of 4-amino-antipyrine. The concentration of 4-amino-antipyrine required to stabilize the peroxidase is between 10 mg to 1000 mg per liter and preferably between 40 mg to 300 mg per liter. In accordance with the most preferred embodiment of this invention, the concentration of 4-amino-antipyrine is from 100 mg to 200 mg per liter.

The following Example illustrates the present invention:

EXAMPLE 0.1 mg/l of (goat) anti-CEA-peroxidase conjugate is dissolved in 0.2 mol/l of sodium phosphate buffer of pH 6.5 with 2 g/l of bovine serum albumin, 20% of normal goat serum (inactivated at 56°/30 min.) as well as 0.5 g/l of "Thimerosal" (Fluka). This anti-CEA-peroxidase solution is divided into two portions. To one portion of this anti-CEA-peroxidase solution is added 0.2 g/l of 4-amino-antipyrine. The two anti-CEA-peroxidase solutions are sterile-filtered (filter: $0.2\mu$) and filled in fractions of 20 ml into sterile glass flasks having a screw closure. These anti-CEA-peroxidase solutions are stored at 2°-8° C. or at 37° C.

After fixed time intervals, the peroxidase activity in the individual anti-CEA-peroxidase solutions is determined by admixing 0.050 ml of the particular anti-CEA-peroxidase solution (pre-diluted 1:20 in 9 g/l of NaCl) with 0.5 ml of substrate buffer solution (0.1 mol/l of sodium citrate of pH 5.0 with 6 mmol/l of $H_2O_2$ and 40 mmol/l of o-phenylenediamine) and then incubating the mixture at room temperature for 15 minutes. The peroxidative reaction is stopped by the addition of 2.0 ml of 1 N HCl and the absorption difference ($\Delta A_{492}$ $nm/RT/15$ $min.$) is measured photometrically. In order to determine the stabilizing effect of the 4-amino-antipyrine, the percentage residual activity of the anti-CEA-peroxidase solution stored at 37° C. is calculated in comparison to that which has been stored at 2°-8° C.

The following Table summarizes the results of the experiment described above and shows the stabilizing effect of 4-amino-antipyrine.

TABLE

| | Percentage residual activity of the peroxidase after: | | | | |
|---|---|---|---|---|---|
| | 0 day | 7 days | 14 days | 21 days | 28 days |
| Without 4-amino-antipyrine | 100% | 2% | 0% | 0% | 0% |
| With 4-amino-antipyrine | 100% | 100% | 77% | 62% | 58% |

We claim:

1. A method for the stabilization of peroxidase which is bound to an immunologically active material in a medium containing serum or serum protein, which method comprises adding a stabilizing effective amount of 4-amino-antipyrine to the medium.

2. The method according to claim 1, wherein the peroxidase is horseradish peroxidase.

3. The method according to claim 1 or claim 2, wherein the serum is goat serum.

4. The method according to claim 3 wherein 4-amino-antipyrine is added in a concentration of 10 mg. to 1000 mg. per liter.

5. The method according to claim 4, wherein 4-amino-antipyrine is added in a concentration of 40 mg. to 300 mg. per liter.

6. The method according to claim 5, wherein 4-amino-antipyrine is added in a concentration of 100 mg. or 200 mg. per liter.

7. A stabilized comosition of peroxidase which is bound to an immunologically active material comprising said bound peroxidase and a stabilizing effective amount of 4-amino-antipyrine.

8. The composition according to claim 7, wherein the peroxidase is horseradish peroxidase.

9. The composition according to claim 8 or claim 9, wherein the serum is goat serum.

10. The composition according to claim 9 wherein the concentration of 4-amino-antipyrine is 10 mg. to 1000 mg. per liter.

11. The composition according to claim 10, wherein the concentration of 4-amino-antipyrine is 40 mg. to 300 mg. per liter.

12. The composition according to claim 11, wherein the concentration of 4-amino-antipyrine is 100 mg. or 200 mg. per liter.

* * * * *